United States Patent [19]

Lörincz et al.

[11] 4,108,996
[45] Aug. 22, 1978

[54] (−)-APOVINCAMINOL LAURIC ACID ESTER AND CEREBRAL VASODILATORY COMPOSITION THEREOF

[75] Inventors: Csaba Lörincz; Maria Bolyos; Kálmán Szász; Laszlo Szporny; Egon Karpati; Eva Palosi, all of Budapest, Hungary

[73] Assignee: Richter Gedeon Vegyeszeti Gyar Rt., Budapest, Hungary

[21] Appl. No.: 703,207

[22] Filed: Jul. 7, 1976

[30] Foreign Application Priority Data

Jul. 18, 1975 [HU] Hungary .................. RI 573

[51] Int. Cl.² .................. A61K 31/445; C07D 519/04
[52] U.S. Cl. .................. 424/256; 260/293.53; 260/293.55
[58] Field of Search .................. 260/293.53; 424/267, 424/256

[56] References Cited

U.S. PATENT DOCUMENTS 4,065,458  12/1977  Lorincz ............ 260/293.55

FOREIGN PATENT DOCUMENTS 2,117,796  9/1972  France ............. 260/293.53
2,035,784  12/1970  France.
2,153,377  6/1972  Fed. Rep. of Germany ...... 260/293.53

OTHER PUBLICATIONS

Morrison et al., "Organic Chemistry", 2nd Ed., Allyn and Bacon, Inc., Boston, (1966).
Chemical Abstracts, 77:105597t, (1972).
Chemical Abstracts, 78:102019n, (1973).

Primary Examiner—Henry R. Jiles
Assistant Examiner—Richard A. Schwartz
Attorney, Agent, or Firm—Karl F. Ross

[57] ABSTRACT

Apovincaminol ester of formula

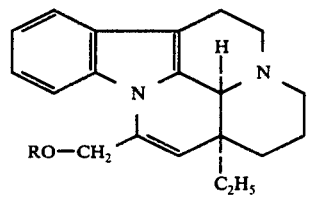

wherein R is an alkylcarbonyl group having 3 to 12 carbon atoms, or a pharmaceutically acceptable acid addition salt thereof.

2 Claims, No Drawings

(−)-APOVINCAMINOL LAURIC ACID ESTER AND CEREBRAL VASODILATORY COMPOSITION THEREOF

The invention relates to the preparation of alkaloid derivatives of the formula I

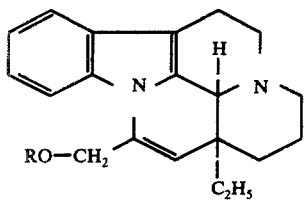

wherein R is an alkylcarbonyl group having 3 to 12 carbon atoms, and of acid addition salts thereof.

The compounds of the formula I are the acylated derivatives of the known apovincaminol, wherein the acyl group is derived from aliphatic carboxylic acids having 3 to 12 carbon atoms.

As acyl group R, the compounds of the formula I may contain any straight or branched chain alkylcarbonyl group, for instance a propionyl, isopropionyl, butyryl, isobutyryl, valeryl, isovaleryl, hexanoyl, heptanoyl, octanoyl, nonanoyl, decanoyl, undecanoyl or lauroyl group.

The French patent specification No. 2,035,784 describes the preparation of apovincaminol and of three related compounds, namely the 14-deoxy-vincaminol, acetylated 14-deoxy-vincaminol and an aldehyde derivative of 14-deoxy-vincaminol. This very limited disclosure of four compounds includes a single acylated compound (the said acetyl derivative of 14-deoxy-vincaminol). The French patent does, however contain a much broader general formula which includes, among others, all acylated derivatives of 14-deoxy-vincaminol and of 6-deoxy-vincaminol and also all acylated derivatives of apovincaminol, without actually describing or even mentioning a single compound of the latter type. The cited specification says further that all compounds covered by the said very broad general formula are therapeutically useful; they are said to act on the coronary artery and on the central nervous system, but this statement is not supported by any pharmacological data or clinical experience.

We have now found that the compounds of apovincaminol formed with aliphatic carboxylic acids having 3 to 12 carbon atoms or with derivatives of such carboxylic acids apt for acylation reactions have excellent cerebral vasodilatatory activity. Apovincaminol carboxylates of this type, though encompassed within the very broadly defined formula I of the said French patent specification, are actually not described, nor even mentioned in the said specification. Their pharmacological properties differ from those of the compounds actually described in the said reference and are outstandingly favorable: their cerebral vasodilatatory activity is several times stronger and more selective than that of the known vincamine which is at present used successfully in this field of therapy.

The pharmacological activity of these new compounds was examined on narcotized dogs. The compounds were administered intravenously to six or eight animals in doses of 1 mg/kg body weight; the average values of the measured effects were expressed in percents of the effect of the reference compound vincamine. The results are summarized in the following table:

| Tested compound | measured effect in percent of the effect of vincamine | | | | |
|---|---|---|---|---|---|
| | (1) | (2) | (3) | (4) | (5) |
| (-)-apovincaminol-propionic acid ester tartrate | 50 | 339 | 136 | 27 | 23 |
| (-)apovincaminol-caprylic acid ester tartrate | 0 | 310 | 210 | 96 | 62.5 |
| vincamine | 100 | 100 | 100 | 100 | 100 |

The columns (1) to (5) in the above table have the following meanings:
(1) decrease of blood pressure;
(2) increase of blood flow in the neck artery (arteria carotis interna);
(3) decrease of the circulation resistance in the cerebral blood vessel region (the quotient of blood pressure and blood flow);
(4) increase of blood flow in the artery of the hind leg (arteria femoralis);
(5) decrease of the circulation resistance in the femoral region.

The blood flow was measured with an electromagnetic flow meter.

The data of the above table show that the effect of the new compounds is directed mainly to the increase of the blood supply of the blood vessel system of the neck artery, and this means the increase of the blood supply of the cerebral region. In this respects the effect of the new compounds exceeds significantly the effect of vincamine. At the same time the new compounds do not influence the blood pressure and the blood flow in the limbs or this influence is much lower than that of vincamine. These results show that the activity of the new compounds is more selective than the activity of vincamine.

The new compounds can be used in therapy for treating various diseases connected with vasoconstriction. They may be administered orally, parenterally or rectally, in the form of free bases or pharmaceutically acceptable acid addition salts. The daily dose may be between 1 mg and 100 mg, preferably between 10 mg and 50 mg, administered in several portions or in the form of a retarded-release composition.

The new alkaloid derivatives of the formula I and the acid addition salts thereof are prepared according to the invention by acylating apovincaminol with an aliphatic carboxylic acid having 3 to 12 carbon atoms or with a reactive derivative thereof, and, if desired, converting the obtained ester of the formula I in known manner into a pharmaceutically acceptable acid addition salt.

As acylating agents, the free carboxylic acids, the anhydrides and, preferably, the halides thereof may be used in the above reaction. The acylation takes places on the primary alcoholic hydroxyl group of the apovincaminol.

Preferably the optically active (−)-apovincaminol is used as starting material in the acylation reaction; the direction of the optical rotation is not changed by the acylation nor by the conversion of the obtained ester into an acid addition salt.

The acylation reaction is performed preferably in an organic solvent, e.g. in a chlorinated hydrocarbon such as dichloromethane or chloroform, or in an aliphatic ketone such as in acetone, or in pyridine. When using an acyl halide as acylating agent, the reaction is performed in the presence of an acid binding agent, e.g. of an alkali metal carbonate or bicarbonate or of an organic base. In the case of using a free aliphatic carboxylic acids as acylating agents, a catalytic amount of an acid, preferably hydrochloric or sulfuric acid or a carboxyl-activating and/or water binding agent is added to the reaction mixture. The carboxyl-activating agent may be a halogenated phenol, preferably pentachlorophenol, and dicyclohexyl carbodiimide may be used as water-binding agent. The acylation reaction can be performed at a temperature between −20° C and the boiling point of the reaction mixture, preferably between 20° C and 60° C.

In a preferred method, the product of the acylation reaction is processed further in the following way:

After the acylation reaction is completed, the pH-value of the reaction mixture is adjusted to 8-9 by adding an aqueous solution of a base, preferably an alkali metal hydroxide; the phases are then separated, the aqueous phase extracted with an organic solvent, preferably with a chlorinated hydrocarbon, the organic phases are combined and evaporated to dryness. The desired product obtained as an evaporation residue may be purified by an adsorption method, preferably by column chromatography on alumina or silica gel.

For this purpose the product may be dissolved in benzene or in an aliphatic alcohol or in a mixture of the solvents; the adsorbed product may be then aluted from the column with the same solvent or solvent mixture. The eluate fractions containing the desired product can be identified by thin layer chromatography; the product is then obtained by combining and evaporating the product containing fractions. The free bases of the formula I are mostly oily substances.

The compounds of the formula I can be converted, if desired, into pharmaceutically acceptable acid addition salts in the usual manner, by reacting them with non-toxic acids. Inorganic acids, as hydrochloric, sulfuric or phosphoric acid, or organic acids, as tartaric, succinic, citric, ascorbic etc. acids may be used for this purpose. The forming of the acid addition salts is performed preferably by adding an ether or acetone solution of the acid to the oily base. The salts are formed at pH values 3 to 5.

The new compounds of the formula I or the pharmaceutically acceptable acid addition salts thereof can be used as active materials of pharmaceutical compositions having a selective cerebral vasodilatatory action. The pharmaceutical compositions can be prepared in forms suitable for oral, rectal or parenteral administration, by mixing the active substance with solid, semi-solid or liquid carriers.

The compositions for oral administration may be prepared in the form of tablets, dragees or capsules in the usual manner, by using e.g. lactose or starch as carrier, gelatine, cellulose derivatives, polyvinyl pyrrolidone or starch paste as binding or granulating material, talc, stearates or colloidal silicic acid as lubricants. The mixture of the active substance and of the above mentioned or other excipients is then granulated and/or pressed into tablets in the usual manner. The tablets may be coated with the usual pharmaceutical coating mixtures to form dragees or the granulated mixture may be filled into hard gelatine capsules.

The suppositories for rectal administration are made by mixing the molten carrier, e.g. vegetable fats, hardened vegetable oils, triglycerides of $C_{12-18}$ fatty acids, and forming from the mass the suppositories in known manner.

Injectable solutions are made by dissolving the active substance in distilled water, lower aliphatic alcohols, glycol ethers or mixtures thereof, if necessary, by the said of solubilizing agents, as polyoxyethylene sorbitan oleate. Preserving agents, as benzyl alcohol or p-hydroxy benzoic acid esters, antioxidants, as ascorbic acid, tocopherol or sodium pyrosulfate, complex-forming substances, buffers and/or other auxiliary materials may be added, if desired, to the injectable solutions.

The preparation of the new compounds of the invention is illustrated in more details by the following non-limiting examples:

EXAMPLE 1

(−)-Apovincaminol-propionic acid ester and the tartrate salt thereof a. 1 g. (0.0032 mol.) of (−)-apovincaminol is dissolved in 7 ml. of dichloromethane and sodium carbonate (in an amount equivalent to the hydrochloric acid liberated in the acylation reaction) is added to the solution and then, while stirring at 20°-25° C, 0.45 g. (0.0048 mol.) of propionyl chloride is added in portions to the mixture. The reaction mixture is stirred then for approximately an hour, and the progress of the reaction is monitored by thin layer chromatography. After the reaction is completed, 10 ml. of 2% aqueous sodium hydroxide solution is added to the reaction mixture and after stirring for 10 minutes the phases are allowed to separate. The organic solvent phase is put aside, the aqueous phase is extracted with 7 ml. of dichloromethane and the separated dichloromethane extract is combined with the original organic solvent phase, dried over potassium carbonate and evaporated to dryness under reduced pressure. The evaporation residue is dissolved in 6 ml. of a 98:2 mixture of benzene and ethanol and chromatographed on a column filled with a 20-fold amount of silica gel of 0.05 to 0.2 mm. particle size. The column is eluted with a 98:2 mixture of benzene and ethanol; eluate fractions of 20 ml. each are collected and the fractions containing the desired (−)-apovincaminol propionate ester (fractions 6 to 13) are combined and evaporated under reduced pressure. The fractions containing the desired product are identified by thin layer chromatography, on silica gel plates, with the solvent system chloroform, ethyl acetate and methanol 8:2:1.

1.06 g. (−)-apovincaminol propionic acid ester (89.0% of theory) is obtained; $R_f = 0.68$ (on silica gel, with chloroform, ethyl acetate and methanol 8:2:1).

A saturated solution of tartaric acid in ether is added to the above obtained oily product until the pH value of 4 is reached. The tartrate salt of the ester begins immediately to precipitate. The mixture is allowed to stand for 12 hours at a temperature between 0° and 5° C, then the obtained crystals are filtered off, washed with 8-10 ml. of cooled ether and dried.

1.15 g. of (−)-apovincaminol propionic acid ester tartrate (69.2% of theory, calculated on the starting apovincaminol) are obtained; m.p. 94°-100° C; $(\alpha)_D^{20} = -48.3°$ (c = 1 in pyridine); $R_f = 0.70$ (on silica gel, with chloroform, ethyl acetate and methanol 8:2:1).

IR spectrum: 3100, 3000 cm$^{-1}$ ($\gamma$ CH aromatic), 3000, 2800 cm$^{-1}$ ($\gamma$ CH$_2$, CH$_3$), 1740 cm$^{-1}$ ($\gamma$ CO ester), 1650 cm$^{-1}$ ($\gamma$ C=C), 1175 cm$^{-1}$ ($\gamma$ COC), 740 cm$^{-1}$ ($\gamma$ CH).

Analysis for $C_{27}H_{34}N_2O_8$: calculated: C 63.1%, H 6.6%, N 5.4%; found: C 63.0%, H 6.5%, N 5.4%.

b. 1 g. (0.0032 mol.) of (—)-apovincaminol is dissolved in 10 ml. of dichloromethane and 0.5 g. (0.0038 mol.) of propionic acid anhydride is added at 20° C to 25° C to the stirred solution. The stirring is continued for an hour, then the reaction mixture is worked up as described in section a) above.

1.05 g. (—)-apovincaminol propionic acid ester tartrate (63–2%) is obtained; the physical properties of the product are the same as in section (a) above.

c. 0.16 g. (0.0005 mol.) of (—)-apovincaminol is dissolved in 3 ml. of acetone; 0.05 g. (0.0006 mol.) of propionic acid are added to the solution and then hydrochloric or sulfuric acid is added to reach a pH value between 2 and 3. The reaction is refluxed for 8 to 10 hours under an inert gas atmosphere. After the reaction is completed, 2% aqueous sodium hydroxide solution is added until pH 8 to 9 and then the mixture is extructed with 3 × 10 ml. of dichloromethane. The dichloromethane phases are combined, dried over potassium carbonate, filtered and evaporated under reduced pressure. The evaporation residue is purified by column chromatography, as described in Example 1.

0.07 g. (—)-apovincaminol propionic acid ester (37%) are obtained, with the same physical properties, as in section a) above.

EXAMPLE 2

(—)-Apovincaminol caprylic acid ester tartrate 1 g. (0.0032 mol.) of (—)-apovincaminol is dissolved in 7 ml. alcohol-free chloroform. Sodium carbonate is added to the solution in an amount equivalent to the hydrochloric acid liberated in the acylation reaction, and then 0.62 g. (0.0038 mol.) of caprylic acid chloride is added in portions to the mixture stirred at 20° to 25° C. The reaction mixture is processed further as described in section a) of Example 1, with the difference that the desired product is extracted with chloroform instead of dichloromethane from the reaction mixture, and 30 ml. fractions of the eluate are collected in the chromatographic purification; the desired product is present in the fractions 7 to 11.

0.93 g. of (—)-apovincaminol caprylic acid ester tartrate (49.1%) is obtained; m.p. 85°–88° C; $[\alpha]_D^{20}$ = —41.2° (c = 1, in pyridine); $R_f$ = 0.75 (on alumina plate, with benzene-acetonitrile 10:1).

IR-spectrum: 3100, 3000 cm$^{-1}$ ($\gamma$ CH), 3000, 2800 cm$^{-1}$ ($\gamma$ CH$_2$, CH$_3$), 1740 cm$^{-1}$ ($\gamma$ C=O ester), 1160 cm$^{-1}$ ($\gamma$ COC), 740 cm$^{-1}$ ($\gamma$ CH).

Analysis for $C_{32}H_{44}N_2O_8$: calculated: C 65.8%, H 7.5%, N 4.8%; found: C 65.6%, H 7.4%, N 4.7%.

EXAMPLE 3

(—)-Apovincaminol lauric acid ester tartrate 1 g. (0.0032 mol.) of (—)-apovincaminol is dissolved in 10 ml. of dichloromethane. Sodium carbonate is then added in an amount equivalent to the hydrochloric acid liberated in the acylation reaction, and then 1 g. (0.0045 mol.) of lauric acid chloride is added in several portions, under stirring at 20° to 25° C. After the addition of lauric acid chloride is completed, the reaction mixture is stirred for an additional 2 hours. The progress of the reaction is monitored by thin layer chromatography. After the reaction is finished, 20 ml. of aqueous 2% sodium hydroxide solution are added to the reaction mixture, which is stirred for 10 minutes and is then allowed to stand in a separating funnel until the phases separate. The dichloromethane phase is then separated and the alkaline aqueous phase is extracted with 10 ml. of dichloromethane. The dichloromethane phases are combined, dried over potassium carbonate, filtered and the filtrate is evaporated to dryness under reduced pressure. The evaporation residue is dissolved in 10 ml. of benzene, and chromatographed on a column filled with an 50-fold amount of alumina (activity: III). The eluation is performed with benzene; fractions of 20 ml. each are collected. The fractions containing the desired ester are identified by thin layer chromatography; the product is obtained in the 5$^{th}$ to 13 fractions. These fractions are combined and evaporated to dryness at reduced pressure. 1.29 g. of the lauric acid ester of (—)-apovincaminol are obtained; this product is converted into the tartrate salt by the method described in Example 1.

1.34 g. of (—)-apovincaminol lauric acid ester tartrate (64.4%) are obtained; m.p. 78°–82° C; $[\alpha]_D^{20}$ = 39.2° (c = 1, in pyridine); $R_f$ = 0.77 (on alumina plate, with 10:1 mixture of benzene and acetonitrile.

IR spectrum: 3100, 3000 cm$^{-1}$ ($\gamma$ CH aromatic), 3000, 2800 cm$^{-1}$ ($\gamma$ CH$_2$, CH$_3$), 1740 cm$^{-1}$ ($\gamma$ C=O), 1650 cm$^{-1}$ ($\gamma$ C=C), 1220 cm$^{-1}$ ($\gamma$ COC), 728 cm$^{-1}$ ($\gamma$ CH).

Analysis for $C_{36}H_{52}N_2O_8$: calculated: C 67.4%, H 8.1%, N 4.4%; found: C 67.3%, H 8.0%, N 4.3%.

EXAMPLE 4

(—)-Apovincaminol propionic acid ester phosphate 0.37 g. (0.001 mol.) of (—)-apovincaminol propionic acid ester is dissolved in 2 ml. of acetone. The pH value of the solution is adjusted to between 4 and 5 by adding the mixture of 1 ml. of concentrated phosphoric acid and 1 ml. of acetone. The mixture is allowed to stand for 12 hours at a temperature between 0° and 2° C. The precipitated phosphate salt is filtered off, washed with 1 ml. of cooled acetone and dried. 0.23 g. of (—)-apovincaminol propionic acid ester phosphate (48% of theory) are obtained; m.p. 211°–214° C; $[\alpha]_D^{20}$ = —74.1° (c = 0.21, in methanol); $R_f$ = 0.70 (on silica gel, with the 8:2:1 mixture of chloroform, ethyl acetate and methanol).

EXAMPLE 5

Pharmaceutical composition in the form of tablets

The following ingredients are used for 1000 tablet:

| | |
|---|---|
| (-)-apovincaminol propionic acid ester tartrate | 5 g. |
| gelatine | 3 g. |
| magnesium stearate | 2 g. |
| talc | 5 g. |
| potato starch | 40 g. |
| lactose | 95 g. |

The active substance is mixed with ¾ part of the potato starch and the lactose. The obtained mixture is formed to a paste with the aqueous solution of the gelatine and granulated in the usual manner; the granules are dried, the talc, the remaining ¼ part of the potato starch and the magnesium stearate are added thereto and the mixture is pressed to 1000 tablets containing each 5 g. of the active substance.

In similar manner tablets are made same amount of other apovincaminol esters or pharmaceutically acceptable salts thereof, e.g. (—)-apovincaminol caprylic acid ester tartrate as the active substance.

What we claim is:

1. (—) -apovincaminol lauric acid ester or a pharmaceutically acceptable salt thereof.

2. A cerebral vasodilatory composition comprising an effective cerebral vasodilating amount of (—)-apovincaminol lauric acid ester or a pharmaceutically acceptable salt thereof and a pharmaceutically acceptable carrier.

* * * * *